United States Patent [19]

Huda et al.

[11] 4,133,198

[45] Jan. 9, 1979

[54] APPARATUS FOR BENDING LARGE AREA CONSTRUCTION UNITS

[75] Inventors: Josef Huda, Ratingen; Heinrich Coenenberg, Düsseldorf-Rath; Friedhelm Aubry, Velbert, all of Fed. Rep. of Germany

[73] Assignee: Balcke-Dürr Aktiengesellschaft, Ratingen, Fed. Rep. of Germany

[21] Appl. No.: 804,450

[22] Filed: Jun. 7, 1977

[30] Foreign Application Priority Data

Jul. 9, 1976 [DE] Fed. Rep. of Germany ....... 2630896

[51] Int. Cl.² .......................................... B21D 7/024
[52] U.S. Cl. ..................................... 72/321; 72/322; 72/388
[58] Field of Search ................. 72/319, 320, 321, 322, 72/388, 219

[56] References Cited

U.S. PATENT DOCUMENTS

| 1,490,933 | 4/1924 | McCabe | 72/321 |
| 1,535,759 | 4/1925 | Beans et al. | 72/219 |
| 1,935,173 | 11/1933 | Anthony et al. | 72/319 |
| 1,967,162 | 7/1934 | Taylor | 72/219 |
| 2,482,617 | 9/1949 | Green | 72/321 |
| 3,188,848 | 6/1965 | Barrett | 72/320 |

FOREIGN PATENT DOCUMENTS 1452919  4/1971  Fed. Rep. of Germany ............ 72/319

Primary Examiner—Michael J. Keenan
Attorney, Agent, or Firm—Martin A. Farber

[57] ABSTRACT

An apparatus for the bending of large area construction units, particularly of tightly welded tube walls for boiler construction, with a supporting table for that part of the construction unit which is not to be deformed, which is held down at least in the vicinity of the bending zone by means of a moveable press. A pivot table is provided for bending the remaining part of the construction unit, which pivot table is equipped with a slide plate abutting the construction part to be bent. The slide plate is guided freely displaceable relative to the pivot table in the longitudinal direction of the same.

7 Claims, 7 Drawing Figures

APPARATUS FOR BENDING LARGE AREA CONSTRUCTION UNITS

The invention relates to an apparatus for the bending of large area construction units, particularly of tightly welded tube walls for boiler construction, with a supporting table for that part of the construction unit which is not to be deformed, which is held down at least in the vicinity of the bending zone by means of a moveable press, and with a pivot table provided for the bending of the remaining construction unit, which pivot table is equipped with a slide plate engaging on the construction part to be bent.

Bending devices of the previously described type are known in various formations. They altogether present the disadvantage that a bending-off on the predetermined or prescribed position is possible only with large tolerances and that grooves or furrows arise in the construction part during the bending which may not be avoided even with careful work.

The invention is based on the task to produce an apparatus of the introductory described type for the bending of large area construction units, particularly of tightly welded tube walls for boiler construction, by which a bending on the prescribed place is possible while keeping a tolerance of merely 1–2 mm and by its use in no way do grooves or cuts develop in the construction parts to be bent, whereby moreover the bending radius can be adjusted in a simple manner to the respectively existing conditions or proportions under the circumstances.

Starting from a device with a supporting table for that part of the construction unit which is not to be deformed, and with a pivot table provided with a slide plate, the pivot table being for the bending-off of the remaining construction part, this task-setting is solved by the invention in the manner that the slide plate is guided freely displaceable relative to the pivot table in the longitudinal direction of the same.

With this formation in accordance with the invention it is guaranteed that during the bending, in no way do grooves or cuts develop in the construction unit, since the slide plate can shift freely relative to the pivot table, and accordingly during the bending operation lies against the construction part to be bent, whereby relative movements between the construction part to be bent on the one hand and the machine part which performs the bending movement on the other hand are excluded.

In order to be able to adjust the bending radius to the prevailing requirements and characteristics of the construction unit to be bent, according to a further feature of the invention the press piston which fixes and holds the construction unit on the supporting table is provided on its front side with an exchangeable shaped-part corresponding to the respective bending radius prevailing under the circumstances; furthermore for the adjustment of the bending operation to the respective predetermined or prescribed bending radius, the pivot axis of the pivot table is adjustable or settable with respect to the frame as well as also with respect to the slide plate. By this doubled adjustment possibility there is guaranteed that the construction unit which is supported on the slide plate is bent always corresponding to the shaped part which is arranged on the press taking into consideration the thickness of the construction unit, so that, in particular, squeezing, pinching, crushing of the tubular walls are reliably avoided during the bending operation.

A slipping or sliding out of the slide plate from the pivot table guide is prevented with the invention in that the slide plate is suspended on the frame on both sides, respectively, on one chain.

A preferred embodiment form for the adjustment shifting of the pivot axis occurs in accordance with the invention by exchanging or replacement of bearing members, which bearing members on the one hand are arranged in an opening of pivot table flanges and on the other hand in openings of bearing flanges of the frame, and respectively are provided with a bore for a bearing bolt, which bearing bore is arranged corresponding to the desired position of the pivot axis. With this formation it is consequently simply necessary, corresponding to the shaped part which is disposed on the press, to arrange two types of complementary or associated bearing members in the bearing between the pivot table and the frame, which bearing members by the respective position of the bore (for the bearing bolt) formed therein guarantee that the pivot movement which is exerted about the prevailing or respectively used shaped part by means of the slide plate, corresponds exactly to the prescribed bending radius.

With a preferred embodiment form, the ram press is moveable by means of two operating cylinders. The pivot table in accordance with the present invention is horizontally pivoted by means of at least two swinging cylinders which are arranged between the pivot table and the frame.

With the present invention altogether an apparatus for the bending of large area construction units is produced which guarantees the bending precisely at the prescribed or predetermined position and with preservation or maintaining of the prescribed radius, whereby large area construction units also can be bent under an angle relative to its longitudinal direction and the bending can take place under any selected angle between 0 and 90 degrees.

In the drawing an embodiment example of the device according to the invention is illustrated, and indeed shows:

FIG. 6 is a corresponding side view of a bearing member used in the pivot table flanges and FIG. 7 is a partially sectioned side view of the suspension of the slide plate.

Figure 1:
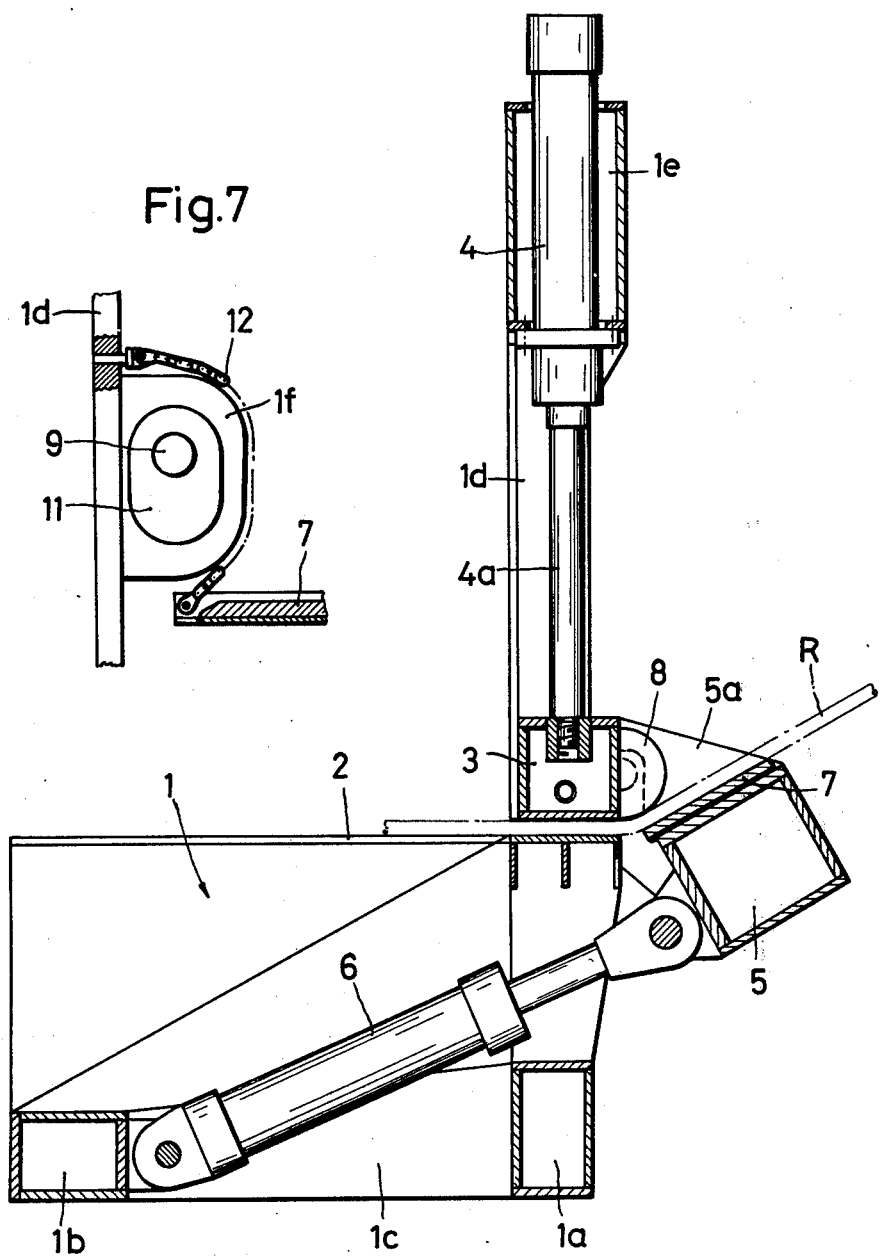
FIG. 1 is a vertical section through the apparatus.
Figure 2:
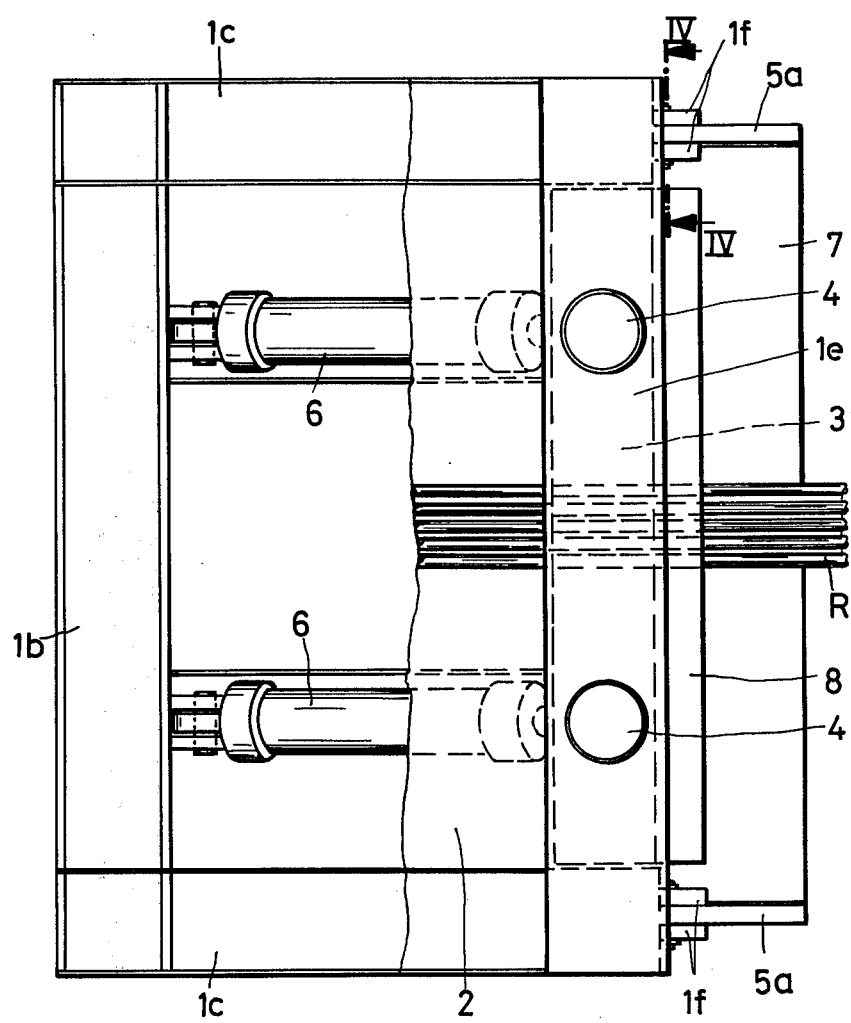
FIG. 2 is a plan view of FIG. 1.
Figure 3:
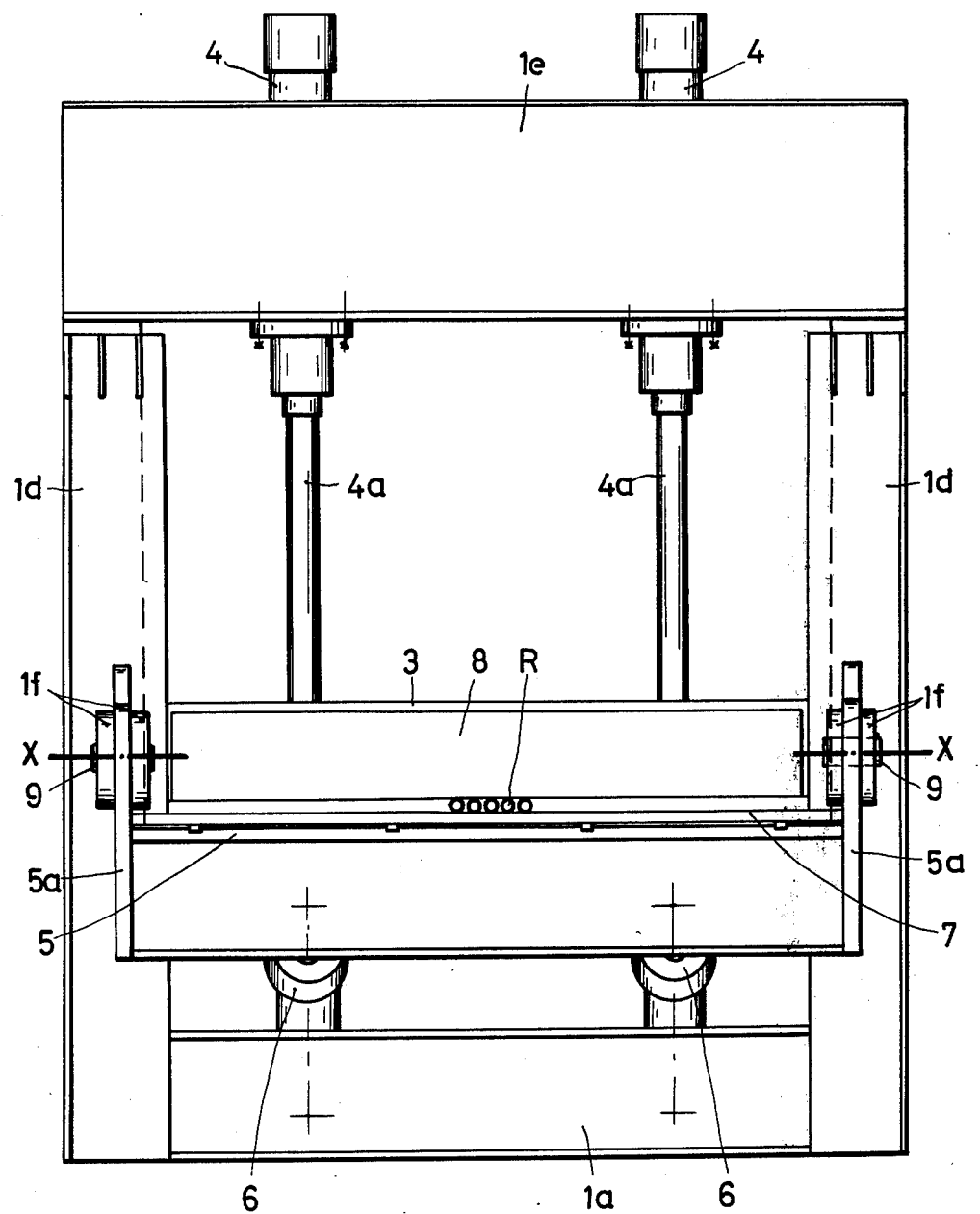
FIG. 3 is a front view of the apparatus in accordance with FIGS. 1 and 2.

The apparatus illustrated in FIGS. 1–3 possesses a frame 1, which with the embodiment example comprises a front crossbeam 1a, a rear crossbeam 1b, longitudinal beams 1c connecting the crossbeams 1a and 1b, and two laterally arranged posts or supports 1d, which supports are connected with one another on their upper ends by means of a transverse 1e. A stationary supporting table 2 is formed on this frame 1, on which table there is laid that part of the construction unit to be worked which is not to be deformed, which construction unit in the illustrated embodiment example comprises a tubular wall R made of tubes which are welded gas-tightly with one another.

This tubular wall R is secured by means of a ram press piston 3 on the supporting table 2, and indeed in the vicinity of the bending zone. The press 3 is moveable by two operating or setting cylinders 4, which are arranged in the transverse 1e and the piston rods 4a thereof are connected with the ram press piston 3.

The part to be bent of the tubular wall R lies on a pivot table 5, which pivot table is horizontally pivotable by means of two swinging cylinders 6, which swinging cylinders 6 are arranged between the frame 1 and the pivot table 5. The pivot table 5 is provided on each of both sides respectively with one pivot table flange 5a. Each pivot table flange 5a is horizontally-pivotally mounted on a bearing bolt 9 between two bearing flanges 1f of the frame 1. These bearing bolts 9 consequently form the pivot axis X—X which is recognized best in FIG. 3.

During the pivot movement of the pivot table 5, in order to prevent a relative movement between the tube wall R on the one hand and the engagement abutment surface of the pivot table 5 on the other hand, a slide plate 7 is freely displaceably guided on the upper surface of the pivot table 5, which slide plate 7 abuttingly engages immoveably on the tubular wall R with its upper surface during the pivot operation and executes a relative movement with respect to the pivot table 5. In this manner tne development of grooves or cuts on the tubular wall R are reliably prevented.

Figure 4:
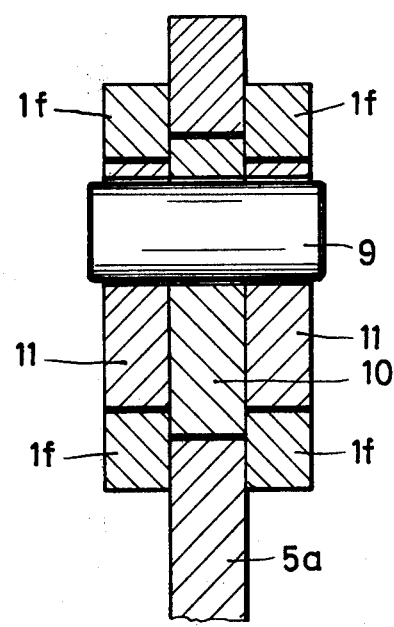
FIG. 4 is a section taken along the section lines IV—IV in FIG. 2 through the bearing of the pivot table on the frame.
Figure 5:
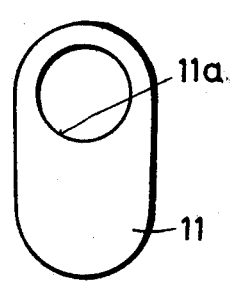
FIG. 5 is a side view of a bearing member used in the bearing flanges of the frame.
Figure 6:
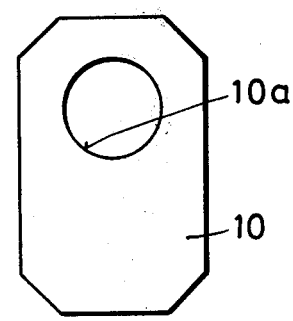

In order to be able to adjust the bending radius of the tubular wall R to the prevailing requirements under the circumstances and moreover in order to exclude a squeezing or pinching of the tube wall R, the pivot axis X—X of the pivot table 5 with respect to the frame 1 as well as also with respect to the slide plate 7 is adjustable or shiftable corresponding to the respectively selected bending radius. This bending radius is preset or predetermined by formed or shaped parts 8, which parts can be exchangeably fastened on the front side of the press 3. The pivot axis X—X formed by the bearing bolts 9 is shiftable or adjustable in the manner that the two bearing bolts 9 respectively are arranged in three bearing members 10 and 11, of which the bearing members 10 lie in an opening of the pivot table flanges 5a, and the bearing members 11 lie in an opening of the bearing flanges 1f. Each of these bearing members 10 and 11 is provided with a bore 10a and 11a, respectively, the arrangement of which provides the desired position of the pivot axis X—X. The previously described construction members are best recognized in FIGS. 4 to 6. This drawing illustration furthermore shows that the bearing member 10 is formed larger than the bearing member 11 so that a lateral slipping out of the bearing member 10 is reliably prevented.

The adjustment or setting of the pivot axis X—X onto the position prescribed by the respectively used shaped parts 8 takes place thus merely by mounting assembly of the bearing members 10 and 11 (which bearing members belong to the prevailing shaped part 8 which is used at the time) in the pivot table flanges 5a as well as also in the bearing flanges 1f. By using correlated construction members, in this way with simple means it is guaranteed that the prescribed predetermined bending radius is preserved and a squeezing of the tubular wall R is prevented.

In order to prevent a slipping-out of the slide plate 7 from the guides of the swinging table 5, as it, for example, could take place with a swinging of the pivot table 5 without a tubular wall R, according to FIG. 7 the slide plate 7 is suspended on both sides, respectively, by means each of one chain 12 on the frame 1. These chains 12 prevent an unintended slipping-out of the slide plate 7 from the pivot table guides, without preventing or hindering the relative movement between the slide plate 7 and the pivot table 5 during the bending process.

We claim:

1. The apparatus for bending large area construction units, in particular tightly welded tubular walls for boiler construction, comprising a frame, a supporting table mounted on said frame and adapted to support a not to be deformed part of a construction unit, moveable pressing means for holding down the not to be deformed part of the construction unit against said supporting table at least in a vicinity of a bending zone, a pivot table means, pivotally mounted relative to said supporting table defining a pivot axis, for bending a remaining part of the construction unit, a slide plate disposed on said pivot table means and abuttingly engaging on the remaining part to be bent of the construction unit, said slide plate is freely displaceably guided with respect to said pivot table in a longitutinal direction thereof transverse to a bending of the bending zone, said pivot table has flanges formed with a first recess, respectively, said frame has bearing flanges formed with second recesses, respectively, bearing members constituting means for adjustment of the pivot axis relative to said supporting table as well as relative to said slide plate by exchange of said bearing members, the latter are exchangeably mounted in said first recesses of said pivot table flanges, respectively, and in said second recesses of said bearing flanges of said frame, respectively, a bore means formed in said bearing members, respectively, and arranged corresponding respectively with one of a plurality of desired positions of the pivot axis, said bore means of said bearing members are aligned when the latter are mounted in said recesses of said flanges, respectively, a bearing bolt disposed in the aligned said bore means of said bearing members defining said pivot axis.

2. The apparatus according to claim 1, further comprising a chain means for connecting said slide plate on both sides thereof, respectively, with said frame.

3. The apparatus according to claim 1, further comprising a shaped part corresponding to a respective radius of bending to be performed exchangeably releaseably mounted on a front side of said pressing means facing towards the remaining part to be bent of the construction unit.

4. The apparatus according to claim 1, further comprising two operating cylinder means for moving said pressing means.

5. The apparatus according to claim 1, further comprising at least two swinging cylinder means for horizontally pivoting said pivot table, said at least two swinging cylinder means are operatively arranged between said pivot table and said frame.

6. The apparatus according to claim 5, wherein said at least two swinging cylinder means are pivotally connected to said frame as well as pivotally connected to said pivot table.

7. The apparatus according to claim 1, wherein said flanges of said pivot table and of said frame, respectively, are laterally arranged at sides thereof constituting two laterally arranged units, each of said laterally arranged units constitutes two of said bearing flanges and one of said pivot table flanges, the latter is disposed between said two of said bearing flanges, and said bearing members mounted in said first recess of said one of said pivot table flanges, respectively, is larger than said bearing members mounted in said second recesses of said two of said bearing flanges, respectively.

* * * * *